US006582078B2

(12) United States Patent
Halpern et al.

(10) Patent No.: US 6,582,078 B2
(45) Date of Patent: Jun. 24, 2003

(54) METHOD AND SYSTEM FOR PLANNING CORRECTIVE REFRACTIVE SURGERY

(75) Inventors: Barton L. Halpern, 175 Delp Rd., Lancaster, PA (US) 17601; Shawn P. Gallagher, Lancaster, PA (US)

(73) Assignee: Barton L. Halpern, Lancaster, PA (US)

( * ) Notice: Subject to any disclaimer, the term of this patent is extended or adjusted under 35 U.S.C. 154(b) by 0 days.

(21) Appl. No.: 09/793,870

(22) Filed: Feb. 27, 2001

(65) Prior Publication Data

US 2002/0154270 A1 Oct. 24, 2002

(51) Int. Cl.[7] ................................................ A61B 3/10
(52) U.S. Cl. ........................................ 351/205; 606/10
(58) Field of Search ................................ 351/205, 206, 351/212, 246; 606/4, 5, 10; 128/920, 923, 898

(56) References Cited

U.S. PATENT DOCUMENTS

| | | | | |
|---|---|---|---|---|
| 4,724,522 A | * | 2/1988 | Belgorod | 606/5 |
| 5,049,147 A | * | 9/1991 | Danon | 606/10 |
| 5,603,709 A | | 2/1997 | Johnson | 606/5 |
| 5,891,132 A | | 4/1999 | Hohla | 606/5 |
| 5,904,678 A | | 5/1999 | Pop | 606/5 |
| 6,004,313 A | | 12/1999 | Shimmick et al. | 606/5 |
| 6,065,043 A | | 5/2000 | Domenikos et al. | 709/203 |
| 6,139,542 A | | 10/2000 | Hohla | 606/5 |
| 6,159,205 A | * | 12/2000 | Herekar et al. | 606/4 |

* cited by examiner

*Primary Examiner*—George Manuel
(74) *Attorney, Agent, or Firm*—Barley Snyder

(57) ABSTRACT

The invention provides a system and method which include receiving inputs from the surgeon based upon patient data and eye measurements, calculating precise corrective settings for laser equipment utilized in the surgery, and outputting the precise corrective settings along with recommendations and cautions for the surgical procedure. It should be understood by those reasonably skilled in the art that the nomograms and formulas described in the invention are dynamic formulas subject to change over time. Changes in the nomogram are required to customize a nonogram for an individual surgeon. In addition, as the art advances, adjustments in the nomograms, including addition and removal of variables, and changes in constants will be required to keep the nomogram consistent with the rapidly evolving state of the art. These changes can be accomplished through upgrades in computer programs. However, it is this very rapidly changing art and changing industry standards, as well as the need to customize nomograms to allow for individual surgeon variability, that make this invention ideally suited for use over the internet.

65 Claims, 5 Drawing Sheets

|  | AGE | | | |
|---|---|---|---|---|
|  | 20 - 30 | 35 - 45 | 45 - 60 | 60 - 75 |
| 0.00 - -1.00 | 0% | 3% | 7% | 13% |
| -1.00 - -3.00 | 1% | 5% | 10% | 15% |
| -4.00 - -6.00 | 5% | 10% | 15% | 20% |
| -7.00 - -9.00 | 9% | 14% | 18% | 25% |
| -10.00 - -12.00 | 12% | 18% | 22% | 28% |
| -13.00 - -15.00 | 15% | 20% | 25% | 30% |
| -16.00 - -18.00 | 20% | 24% | 30% | 36% |

(SPHERICAL EQUIVALENT on vertical axis)

FIG. 1

METHOD AND SYSTEM FOR PLANNING CORRECTIVE REFRACTIVE SURGERY

FIELD OF THE INVENTION

This invention is related to refractive eye surgery, and more particularly to a software tool for assisting surgeons in planning this surgery.

BACKGROUND

Refractive errors result when the optical elements of the eye, namely the cornea and the lens, do not focus a clear image onto the retina. An eye is considered emmetropic if it has no refractive error. Most eyes have at least some degree of refractive error. In myopia, the optical elements are too strong for the length of the eye, and the image is focused in front of the retina. In hyperopia, the optical elements are too weak for the length of the eye, and the image is focused behind the retina. In astigmatism, the optical elements cannot focus an image to a single point, and the image is split and focused at two separate points.

When a refractive error is present, a lens may be used to refocus light onto the retina. This lens may be in the form of a spectacle lens or contact lens. Additionally, a lens surgically implanted within the eye (intrastromal or intraocular) can be used.

The cornea is the strongest refracting lens of the eye. Therefore, small changes in the shape of the cornea result in large changes in the overall refractive properties of the eye. By making the cornea flatter or steeper in a controlled fashion, a surgeon can affect changes in the eye's refractive power. Using mathematical calculations and review of surgical results, a surgeon can predict the amount of refractive change induced by a given amount of corneal reshaping. Surgeons use these calculations to predict the outcome of corneal refractive surgery.

Radial Keratotomy (RK), Arcuate Keratotomy (AK), and Photo Refractive Keratectomy (PRK) are refractive corneal surgical techniques that have been commonly used in the past to induce controlled changes in the shape of the cornea, and subsequently in the refractive error. In RK and AK procedures, surgeons use a diamond-bladed scalpel to make small incisions in the cornea. Radial incisions, used in RK, reduce myopic refractive errors while arcuate incisions, used in AK, reduce astigmatic refractive errors. These incisions induce changes in the corneal curvature and, consequently, alter the eyes' refractive properties.

PRK procedures use a laser to reshape the corneal surface. The laser sculpts a thin layer, between 5 and 10 mm in diameter, on the corneal surface. This technique has many advantages over RK/AK since it usually cuts less than 10 percent of the way through the cornea, as opposed to about 90 percent with RK/AK, and can correct a wider range of myopic, hyperopic, and astigmatic refractive errors.

Laser Assisted In Situ Keratomileusis (LASIK) offers additional advantages over both RK/AK and PRK. The LASIK procedure consists of two distinct surgical procedures. The first part of the procedure involves the surgical creation of a corneal flap. The laser is then used to treat deeper corneal stroma tissue in much the same way as PRK treats the stroma near the corneal surface. The flap is then replaced after the laser treatment. This offers the advantage of leaving much of the corneal surface intact, leading to faster and more comfortable recovery for the patient.

Despite its advantages over other corneal refractive surgery techniques, LASIK refractive surgery still has a number of shortcomings. This invention addresses, among other things, one of these shortcomings, namely, the fact that many excimer lasers now used for LASIK were built for the purpose of performing PRK refractive surgery. Consequently, when a surgeon enters patient data such as refractive error and patient age, the laser calculates a treatment based on the expected results of PRK, not LASIK. Therefore, a surgeon must compensate for the fact that LASIK and PRK differ in refractive treatment effects by making appropriate adjustments to the refractive error information that is entered into the machine. This means that the surgeon often cannot use the patient's actual refractive error to achieve the best surgical result. Instead, the refractive error information that is actually entered must be adjusted by as much as 25 percent in order to optimize the treatment. These adjustments are calculated using a nomogram that is created on the basis of previous surgical results. An example of a nomogram for myopia is shown in FIG. 1. There are different nomograms utilized for each type and combination of refractive errors including myopia, hyperopia, and astigmatism. It should also be understood that these charts are specific to particular surgical laser equipment, and somewhat dependent on variations in surgical technique. Different surgical laser equipment manufactured by different suppliers would therefore require different chart nomograms. The chart nomogram (FIG. 1) has patient age in years on one axis and diopters of refractive error on the other axis. Each axis contains a range for each data entry. Where the x and y-axis meet, a correction percentage is given. This represents the amount that the programmed refractive error must be changed in order to perform LASIK. A problem arises in that a large amount of surgeon judgment is required in utilizing a chart nomogram. This judgment is required because each axis includes range data that will affect the percent correction factor in setting the laser. For example, if the patient is at the low end of an age range on one axis and has a spherical equivalent at the low end of the refractive range on the other axis, the surgeon may adjust the percentage of correction suggested in the chart nomogram by a different amount than if the patient's age or refractive error were at a different point within the same range on the x or y axis. The correction percentage indicates that the refractive laser should be set for the desired diopters of correction by adjusting the spherical refraction. The surgical plan may also include a simultaneous but different formula to adjust the cylindrical portion (astigmatism) of the manifest refraction.

The growing body of clinical evidence suggests that a nomogram must take into consideration a number of factors including but not limited to the refractive error of the eye and the patient's age at the time of surgery. Other parameters may influence the refractive effect of the laser treatment on the eye, including the vertex distance of the refraction, and the patient's gender. Despite this accumulation of data, LASIK, like all surgical procedures, can vary in effectiveness from surgeon to surgeon and from patient to patient. It should be emphasized that, as more information is collected, the nomograms can, and should, be revised to include statistical data indicative of a particular surgeon's procedural results.

The beginning surgeon has no personal surgical data, and therefore cannot predict the effectiveness of an excimer laser, built and programmed for PRK, when used for LASIK. With experience, a surgeon may begin to understand the variables that will result in over- or under-correction, however, with no personal experience; a beginning surgeon must rely on nomograms based on the results of others. What is needed is a tool to assist such surgeons in developing a standardized technique and nomogram based on the results of other surgeons. What follows is a brief review of the decisions a surgeon must make in preparation for LASIK surgery.

LASIK DECISIONS

Refractive Error Correction. One of the most important decisions involves understanding the design of the laser system being used. As stated, many lasers were designed and programmed for the purpose of performing PRK. If a surgeon wishes to perform LASIK using one of these machines, he or she must understand that the programmed correction must be adjusted based on the known differences between PRK and LASIK. These differences are currently addressed using published chart nomograms, however, more precise adjustment calculations would be desirable. Currently, the clinical evidence suggests that age and refractive error have a bearing on the effectiveness of LASIK treatment, but as more data become available, factors such as gender may also be shown to affect LASIK treatment.

Most patients wish to be emmetropic after LASIK surgery. That is, they would like to have both eyes corrected for good distance vision. Younger emmetropic patients, those under forty, have enough accommodative power in their lenses to allow them to focus on near objects. However, this accommodative power is naturally lost with age and individuals usually require glasses for reading and seeing close objects clearly. Older LASIK patients, especially those over age forty, may opt for monovision correction by having each eye corrected differently in order to have one "reading vision eye" and one "distance vision eye." Understanding how to operate on such monovision patients requires that the surgeon determine the patient's dominant eye as well as understand the patient's reading needs. Monovision patients opt to leave one eye, usually the non-dominant eye, slightly nearsighted. This is achieved by intentionally undercorrecting an eye if it is initially myopic or over-correcting an eye if it is initially hyperopic. After surgery, the patient can avoid the need for glasses by shifting attention between eyes depending on the visual task.

Suction Ring Size. The first step of LASIK, creating the corneal flap, is done by fixating the eye using a suction ring. The suction ring also serves to apply controlled pressure to the globe, allowing for a more reproducible corneal flap cut. The surgeon may use a ring size of 8.5 millimeter or 9.5 millimeter or another size, depending on the steepness or flatness of the cornea and on whether the refractive surgery is being done to correct myopia, hyperopia or astigmatism, or a combination of astigmatism together with myopia or hyperopia. A flatter cornea is more reproducibly fixated using a larger diameter ring such as a 9.5-millimeter ring, whereas a steeper cornea is more reproducibly fixated using a smaller ring size such as an 8.5-millimeter ring. A larger ring size and the resulting larger corneal flap has the advantage of better accommodating a possible enhancement in the event of an initial over correction, but has the disadvantage of being more difficult to handle. A larger ring size, such as a 9.5-millimeter ring, is currently recommended for the treatment of hyperopic refractive errors.

Plate Depth. The current state of the art requires the surgeon to select a plate to set the depth of the corneal flap cut, such as a plate of 160 or 180 microns. In making this decision, the surgeon must take into consideration the initial corneal thickness, the refractive error requiring surgical correction, monovision needs if any, patient's age and the optical zone requiring treatment. Additionally, the surgeon may have to take into consideration other parameters, such as the vertex distance that the refraction is performed at, and gender, all of which may affect the depth of laser ablation. In addition, the surgeon must consider industry standards of minimal safe residual corneal bed depth as well as the likelihood of the need for an enhancement, in order to select the optimal plate thickness.

Although examples of plate depths of 160 and 180 microns have been described, it should be noted that the same information applies for cuts at other plate depths, and for developing techniques whereby a laser or other device is focused at a controlled depth to either make the corneal flap cut. Alternatively, the refractive laser or refractive device is itself focused at a controlled depth to perform the refractive surgery.

Unfortunately, residual corneal thickness and flap thickness are both best kept maximally thick, which are mutually exclusive goals. Surgeon judgment is required to select the plate depth that best balances these goals. Surgeon judgement is also required to avoid surgery on a cornea that is too thin for the degree of refractive correction required.

Laser Pulse Frequency. Currently, the surgeon selects the laser's pulse frequency. The higher the frequency, the more rapidly the laser pulses occur, and the shorter the laser treatment time. Quicker laser treatments, in theory, result in fewer variations in corneal thickness due to time-related drying between pulses, and, consequently minimizes variability in refractive results. On the other hand, if high laser frequencies are used to treat small myopic refractive errors, the laser treatment time may be very short, increasing the risk that involuntary eye movements or loss of fixation during laser treatment will have a disproportionately large and undesirable effect.

What is needed is a method to reduce surgeon variability and balance the mutually exclusive needs of rapid treatment to avoid variations in ablation depth due to time related corneal thinning and drying, with the need to have a longer treatment time to minimize abnormal, inefficient and off-center treatment due to patient eye movement.

Patient Cautions. Current surgical standards do not provide surgeons with cautions to reduce adverse visual outcomes, such as those which may result from patients who are too young for surgery, corneas that are too thin for the desired correction, eyes that are excessively dry, pupils that are too large for a given refractive error treatment at a particular optical zone requiring treatment, and other patient-specific variables, such as discrepancies between corneal and refractive astigmatism, or non-patient specific errors such as data entry errors. What is needed is a tool for identifying these risk factors that may lead to an undesirable result.

SUMMARY

It is therefore an object of this invention to provide tools, that assist surgeons in preparing a preoperative plan for refractive eye surgery. This and other objectives are achieved by providing a system and method which provide for receiving inputs from the surgeon based upon patient data and eye measurements, calculating precise corrective settings for the laser equipment utilized in the surgery, and outputting the precise corrective settings along with recommendations for the surgical procedure, including refractive error correction, plate thickness, ring size, and laser frequency. In addition, the system and method provide cautions with respect to a patient's age, tear function, pupil size, corneal thickness, and discrepancies between refractive and corneal astigmatism.

BRIEF DESCRIPTION OF DRAWINGS

The invention will now be described by way of example with reference to the accompanying figures of which:

FIG. 1 is a chart nomogram for myopic refractive errors.

DETAILED DESCRIPTION OF PREFERRED EMBODIMENT

Figure 2:
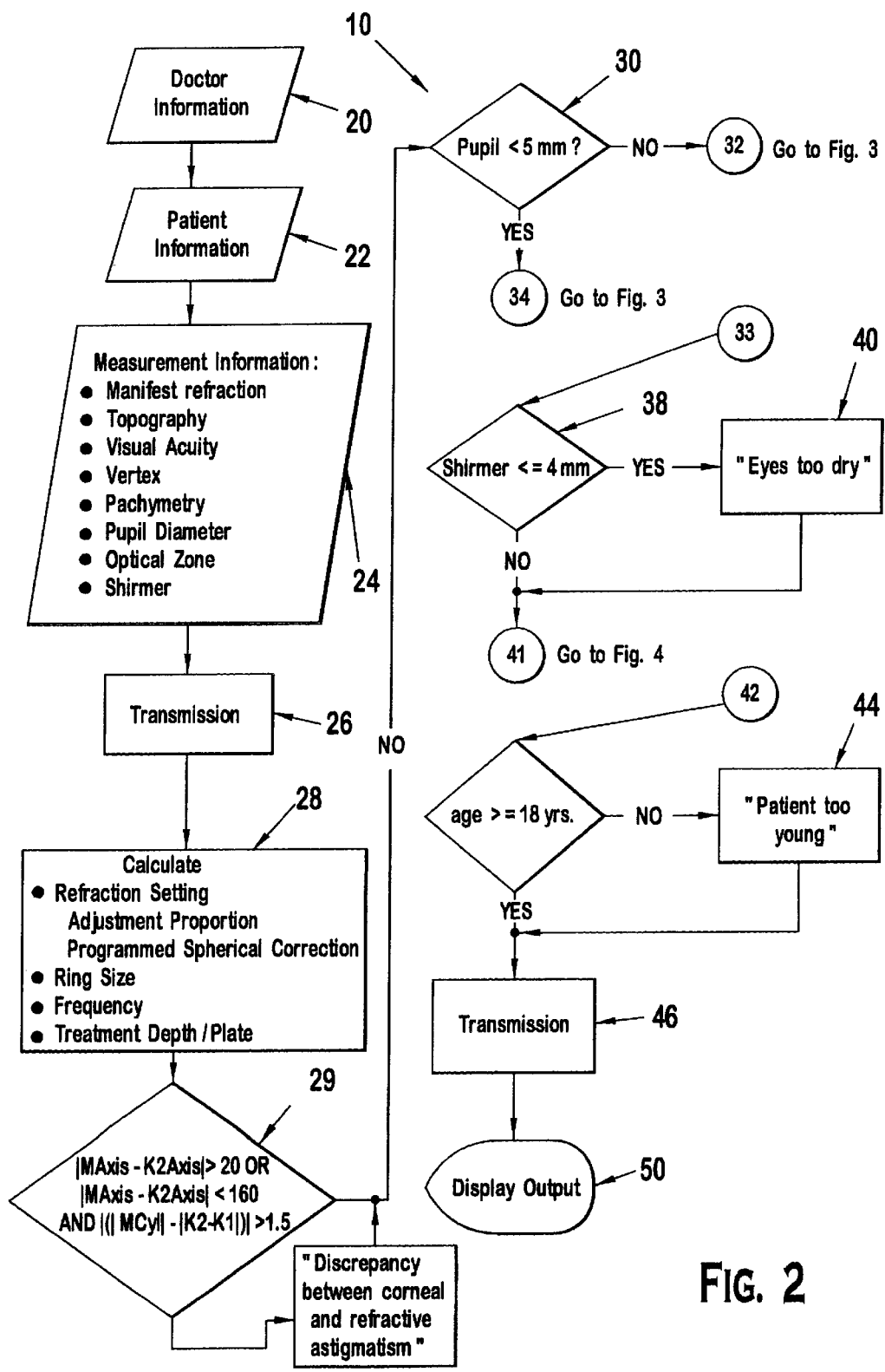
FIG. 2 is a partial flow diagram according to the present invention.

The invention will now be described in greater detail with reference to FIGS. 2–5. A method 10 and system are provided for assisting surgeons in preoperative surgical planning. First, the method will be described and then systems for performing the method 10 will be described. The method 10 includes collecting doctor information at step 20. This information includes the doctor's name and related contact information, which can be stored by the system 10 for marketing or other purposes. Next, at step 22, basic patient information is collected. This information includes the patient's name, gender, date of birth, date of surgery, identification of dominant eye, whether the patient requires monovision and if so, the amount of monovision desired in diopters, and identification of the eye or eyes requiring surgery.

It should be understood by those reasonably skilled in the art that the following description of the invention is presented for use in LASIK eye surgery and that the method is adaptable for use as a preoperative tool for other similar surgical techniques. The surgeon enters a series of measurements taken from each of the eyes requiring surgery. These measurements are input into the method 10 at step 24 and include manifest refraction, corneal topography, visual acuity, vertex distance of corrective lens, thickness of the cornea as measured by pachymetry, pupil diameter, desired optical zone of ablation, Shirmer tear production, and additional comments. The manifest refraction input includes a sphere in diopters and a cylinder in diopters along with the axis of the astigmatism. The corneal topography input includes a numerical description of the corneal curvatures in diopters along with an axis to indicate the direction of the steeper and flatter corneal curvatures. The visual acuity input includes measurements at both distance and near, both with and without a corrective lens. The vertex distance is measured in millimeters of distance separating the corrective lens from the cornea. The corneal thickness input is entered in microns as measured by pachymetry. The pupil diameter input is entered in millimeters. The optical zone input identifies the diameter of the area to be treated by the laser ablation procedure in millimeters. Finally, Shirmer tear production is measured and entered in millimeters of wetting during a five minute period of time.

The following variables for the inputs and calculated data will be utilized in formulas below:

| Variable Name | Represents |
|---|---|
| Age | Patient age in years |
| K1 | Power of Primary Keratometric Curvature |
| K2 | Power of Secondary Keratometric Curvature |
| K Axis | Direction of K2 |
| Manifest Axis | Axis of astigmatism in manifest refraction |
| Manifest Cyl | Power of manifest cylinder in Diopters |
| Manifest Sphere | Power of manifest sphere in Diopters |
| Monovision Power | Degree of undercorrection for monovision in Diopters |
| Negative Cylinder Cylinder | Cylinder in negative cylinder format |
| Negative Cylinder Sphere | Sphere in negative cylinder format |
| Pupil | Pupil Size in millimeters |
| RSB | Residual Stromal Bed |
| Schirmer | Result of Schirmer Tear Test in millimeters per 5 minutes |
| SERE | Spherical equivalent refractive error |

At step 26, the method includes transmission of this data to a processing device, 64 (FIG. 3), where calculations are performed at step 28. Calculations are performed to determine distance and/or near refraction, recommended ring size, recommended laser frequency, and plate thickness. It should be understood by those reasonably skilled in the art that this method will be described preferably for the use of the VISX-Star-S2 surgical laser equipment. However, based upon nomograms provided for similar equipment manufactured by other manufacturers, the following method and formula may be adapted for each surgical laser, and for other devices that set ablation depth and alter corneal contour.

A precise distance refraction is utilized as the set point for the surgical laser with the refraction corrected by an amount determined by a refractive nomogram for sphere, cylinder, and axis. Because most of the Excimer lasers were originally used for the purpose of performing PRK, and because the effective treatment dose differs between PRK and LASIK treatments, the surgeon must adjust the programmed treatment based on a nomogram that compensates for this difference. For example, whereas a particular degree of laser treatment may result in 2.0 diopters of correction in a PRK procedure, the same treatment may result in 1.75 diopters of correction with a LASIK procedure. Because many excimer lasers calculate treatment dosages based on PRK parameters, the surgeon must adjust the programmed treatment for LASIK procedures. This involves reducing or increasing the programmed amount of refractive error to match the actual results that the procedure will induce with a given laser. The following equation generates a Proportional Adjustment that corrects the excimer laser's PRK calculations for LASIK. The equation for this adjustment proportion is as follows:

IF: Manifest Sphere<0.0 Diopters

Then: Adjustment Proportion=[100−(Age(0.365)+SERE(−1.22)−10.75)]/100

Otherwise: Adjustment Proportion=(100+(−0.16)Age−(2.76)Manifest Sphere+29.64)/100

These proportional correction formulas were generated by the inventor using a statistical analysis of his own surgical results, however the invention is intended to be adapted, through it's use, to modify these proportional correction formulas based on statistical analysis of the user's results. It should be noted that this formula for proportional adjustment utilizes exact patient age and exact spherical and cylinder inputs, as opposed to range data used in chart nomograms of the prior art shown in FIG. 1. The output is therefore more precise and requires no adjustment for input ranges.

The spherical portion of the patient's refractive error is multiplied by this proportion in order to generate the actual spherical correction to be programmed into the excimer laser as follows:

Programmed Spherical Correction=Adjustment Proportion (Negative Cylinder Sphere)

This equation is modified in the event of monovision as follows:

Programmed Spherical Correction=Adjustment Proportion (Negative Cylinder Sphere+Monovision Power)

The cylindrical, or astigmatic, portion of the refractive error is adjusted by the same proportion if it is greater than 2.0 Diopters as follows:

IF: Manifest_Cyl>2.0 Diopters

Then: Programmed Cylindrical Correction=Adjustment Proportion (Negative Cylinder Cylinder)

Otherwise: Programmed Cylindrical Correction= Negative Cylinder Cylinder

The cylindrical portion of the programmed refractive error correction requires no additional adjustment for monovision.

As shown in FIG. 2 step 29, an additional nomogram generates a caution if there is either a discrepancy between the refractive and corneal astigmatism of greater than 2 diopters in magnitude, or greater than 20 degrees in axis as follows:

IF: |(Manifest Axis−K2 Axis)|>20 OR |(Manifest Axis−K2 Axis)|<160

AND: |(|Manifest Cylinder|−|K2−K1|)|>1.5

THEN: Generate "Caution: Discrepancy between corneal and refractive astigmatism" message.

OTHERWISE: Generate "Proceed" message

The ring size recommendation is based upon a separate nomogram comparing corneal topographic measurements with industry recommendations, to suggest the ring size most likely to yield optimal suction for creation of the corneal flap. A flat cornea is best grasped by suction applied through a larger ring, such a 9.5-millimeter ring. A steep cornea is best grasped by suction applied through a smaller ring, such a 8.5 millimeter ring. Industry standards are used to determine whether a cornea is flat or steep, based on corneal topography measurements. Suction applied through the ring is used to fixate the eye and to raise the pressure in the eye so as to allow a more reproducible creation of the corneal flap. In addition, a larger ring size such as a 9.5-millimeter ring size is recommended for hyperopic refractive corrections. It should be understood by those reasonably skilled in the art that the following description of the invention is presented for use utilizing rings of 9.5 and 8.5 millimeter sizes, and that the method is adaptable for use as a preoperative tool for other inputs. The following routine is utilized to determine ring size:

IF: Negative Cylinder Sphere>0.0 Diopters OR K1<42

THEN: Use a 9.5 mm ring

OTHERWISE:
  IF: K1<=45.0
  THEN: Use a 9.5 or 8.5 mm ring
  OTHERWISE: Use a 8.5 mm ring The laser frequency reflects the time it takes to ablate the desired amount of corneal surface. If the eye moves during treatment, the laser may impinge on areas outside of the desired optical treatment zone and therefore ablation may occur in an undesirable pattern. At lower frequencies, particularly in eyes with large refractive errors, the ablation time is longer and therefore a greater amount of corneal drying time and thinning may occur, resulting in excessive laser treatment. On the other hand, at higher frequencies, particularly in eyes with small refractive errors, involuntary eye movements may represent a disproportionate amount of the laser treatment time and result in under treatment of the optical zone requiring treatment, or an abnormal treatment pattern. In general, hyperopic treatments take longer than treatment times for comparable myopic refractive errors, and therefore usually performed at a higher frequency. In general, it is desirable to minimize the time required to conduct the procedure after the flap has been lifted, and therefore in general it is desirable to increase the frequency to a degree which minimizes the laser treatment time, while on the other hand balancing the risk of an undesirable ablation during an involuntary eye movement. A laser frequency recommendation is based on a separate nomogram comparing refractive error and treatment time and is calculated as follows:

IF: SERE>0 AND SERE<−1.75

THEN: Frequency=10 Hz

OTHERWISE: Frequency=−4.5 (SERE)+2.0

The plate depth is determined by a separate nomogram which calculates the residual corneal bed based on the refractive error, monovision needs if any, optical treatment zone size, preoperative corneal thickness as measured by corneal pachymetry, and the variables of a plate depth of either 160 microns or 180 microns. Refractive surgery has evolved to the point that surgeons in general feel that optimal visual and refractive results, patient comfort, refractive stability, and visual recovery are enhanced by performing laser refractive surgery within the cornea rather than on the surface of the cornea. The surgeon tries to balance the desires for a maximal residual corneal stromal bed depth, with a maximal corneal flap thickness, desires which are mutually exclusive. This separate nomogram allows the surgeon to select the plate depth, which will best balance these variables. It should be understood by those reasonably skilled in the art that the following description of the invention is presented for use utilizing a plate thickness of 160 microns and 180 microns, and that the method is adaptable for use as a preoperative tool for other inputs of plate thickness and for other methods of causing ablation to occur at a desired corneal stromal depth. The following routine is utilized to determine plate thickness:

IF: Residual Stromal Bed at 180 plate depth>250

THEN: Use 180 micron plate thickness

OTHERWISE:
  IF: Residual Stromal Bed at 180 plate depth<250 and Residual Stromal Bed at 160 plate depth>250
  THEN: Use 160 micron plate thickness
  ELSE: Plate thickness cannot be determined Next, a number of checks are performed for various conditions, which may prevent or adversely affect the outcome of the surgical procedure. First, at step 30, a test is performed for pupil size. In situations where a large refractive error correction is necessary, the optical zone and ablation depth will be large. A relatively large pupil in combination with such a large refractive error correction may result in the patient suffering from glare following surgery. The refractive error and pupil size are therefore compared according to a separate nomogram formula which provides the surgeon with cautions and guidance in recognizing this potentially disabling outcome and avoiding it, minimizing it, and or counseling the patient as to the likeliness of this outcome in advance of surgery. First, a risk factor is calculated based on the degree of myopia corrected to the spherical equivalent refractive error form, and pupil size. This risk factor is generated based on the inventor's personal results and may be adapted to the statistical results of a given user accordingly. Beginning at step 30 in FIG. 2 and continuing to FIG. 3, the following routine is utilized to determine glare risk:

IF: Pupil<5.0
THEN: Glare Risk=0
OTHERWISE: Glare Risk=1.1(Pupil)+0.47(−SERE)−6

Figure 3:
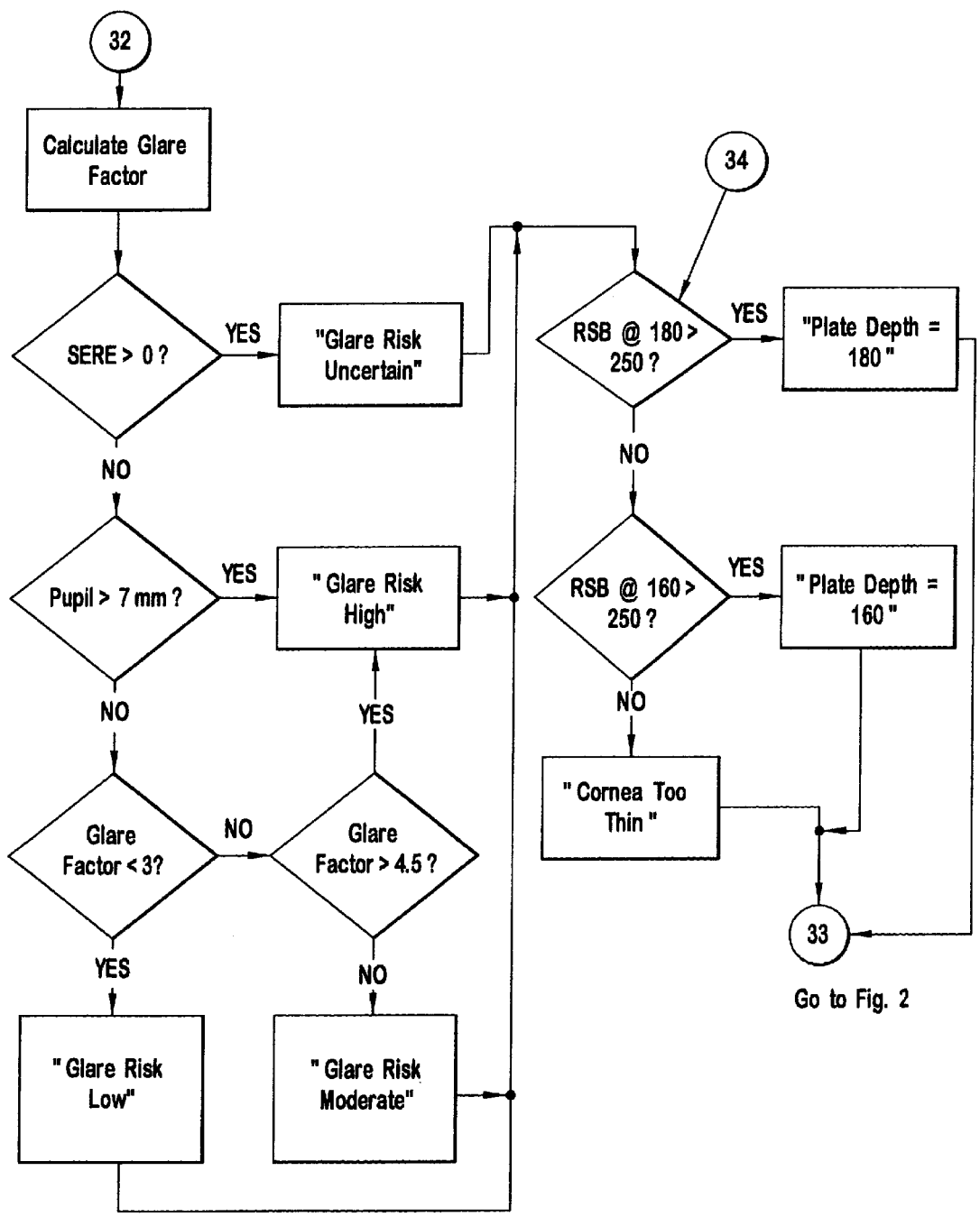
FIG. 3 is a partial flow diagram showing glare risk and plate depth subroutines.
Figure 4:
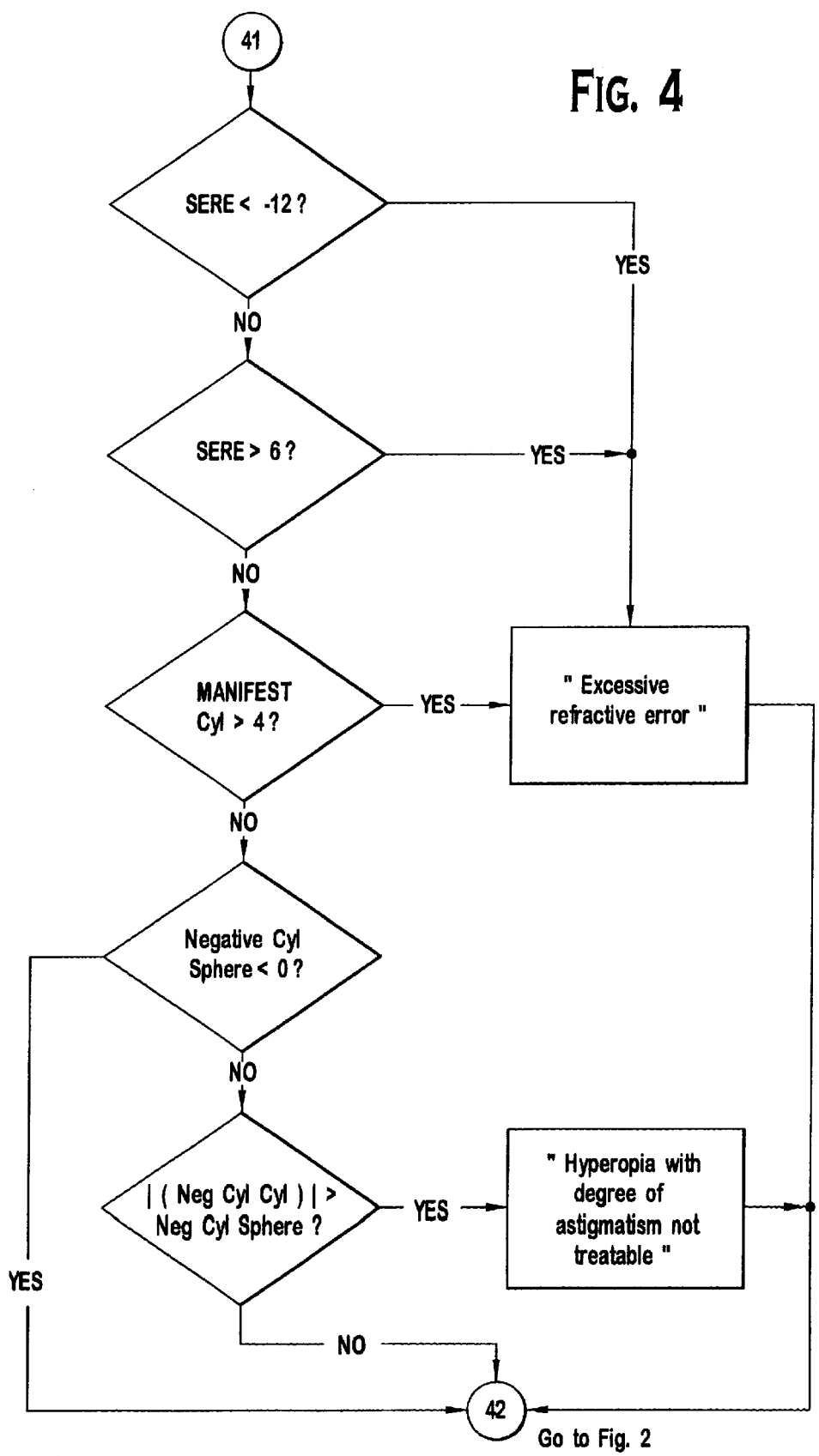
FIG. 4 is a partial flow diagram showing additional caution subroutines.

As shown in FIG. 3, the following cautions are then generated based on the pupil size and resulting glare risk factor.

IF: SERE>0,
THEN: Generate "Glare risk uncertain" message
OTHERWISE:
  IF: Pupil>7.0
  THEN: Generate "Stop: Glare risk is high since pupil may be too large" message
  OTHERWISE:
    IF: Glare Factor<3
    THEN: Generate "Proceed: Glare risk low" message
    OTHERWISE:
      IF: Glare Factor>4.5
      THEN: Generate "Stop: Glare risk high" message
      OTHERWISE: Generate "Glare risk moderate" message If the nomogram suggests that the pupil may be too large for a given refractive error and possibly optical treatment zone, then a caution indicating that the pupil is too large is flagged as shown in FIG. 3.

At step 34, FIG. 3, an additional nomogram is used to compare the refractive error, monovision needs if any, optical treatment zone size, preoperative corneal thickness as measured by corneal pachymetry, and flap thickness to determine whether there will be enough residual corneal thickness to safely conduct the surgery. The comparison is represented by the following nomogram formula:

IF: RSB AT 180 DEPTH>250
THEN: 180
OTHERWISE:
  IF: RSB AT 180 DEPTH<250 AND RSB AT 160 DEPTH>250
  THEN: 160
  OTHERWISE: Generate "STOP—Cornea may be too thin for this degree of myopia" message Current industry standards suggest that the residual corneal bed thickness after laser treatment should be at least 250 microns. If the calculations indicate that if the surgeon uses a plate depth of 180 microns, the residual corneal bed depth following laser treatment will be less than 250 microns, then the formula next calculates the ablation using a 160 micron plate to allow a thicker residual corneal bed depth. If the corneal bed depth will be less than 250 microns following the surgery with either plate, then a caution indicating that the cornea is too thin is flagged at step 36.

At step 38, FIG. 2, if the Shirmer tear production is less than 4 millimeters of wetting, then a caution that the eye may be too dry is flagged at step 40 as follows:

IF: Schirmer>4.0
THEN: Generate "Proceed" message
OTHERWISE: Generate "CAUTION—Eyes may be too dry" message Another check is performed at step 41, FIG. 4 to make sure that the patient's refractive error falls within the treatable parameters established by the FDA. These parameters state that:

1. A patient may not be treated for more than −12.0 spherical equivalent diopters of myopia.
2. A patient may not be treated for more than +6.0 Diopters of spherical equivalent hyperopia.
3. A patient may not be treated if for more than 4.0 Diopters of astigmatism.
4. A hyperopic patient may not be treated if the Diopters of astigmatism exceed Diopters of hyperopia.

Restrictions 1–3 are applied at step 29 with the following equation:

IF: SERE<−12.0 Diopters OR SERE>6.0 Diopters OR Manifest Cyl>4.0 Diopters
THEN: Generate "STOP—Excessive refractive error" message
OTHERWISE: Generate "Proceed" message Restriction 4 is applied with the following equation:

IF: Negative Cylinder Sphere<0
THEN: Generate "Proceed" message
OTHERWISE:
  IF: |Negative Cylinder Cylinder|>Negative Cylinder Sphere
  THEN: Generate "STOP—Hyperopia with this degree of astigmatism is not currently treatable" message
  OTHERWISE: Generate "Proceed" message An age check is performed at step 42, FIG. 2, to flag a caution that the patient is too young at step 44 if the patient age is less than 18 years of age at the time of surgery. The patient's age is calculated in step 12 by subtracting the surgery date gathered in step 22 from the patient date of birth also gathered in step 22 as follows:

IF: Age>=18
THEN: Generate "Proceed" message
OTHERWISE: Generate "STOP—Patient may be too young" message At step 46, the calculation results from step 28, and any of the flagged cautions from steps 32, 34, 40, 41 or 44 are transmitted back to the user as display output at step 50.

Although this method provides recommended laser settings and procedural recommendations, outcomes may vary depending upon the individual surgeon's technique. For example, the time required to complete the procedure once the flap has been lifted may vary from surgeon to surgeon. This time variation may still result in varying outcomes due to time related drying and thinning of the exposed corneal stoma bed. This system 10 and method may alternately collect outcome data for each patient and then based upon the statistics of a number of procedures performed by a given surgeon, many vary the calculations presented above (e.g. customize the nomogram) in order to compensate for a surgeon's individual technique. For example, if a particular surgeon performs the surgery in a comparatively short period of time, the calculations can be adjusted accordingly to give laser settings that are more likely to achieve the precisely desired outcome.

Figure 5:
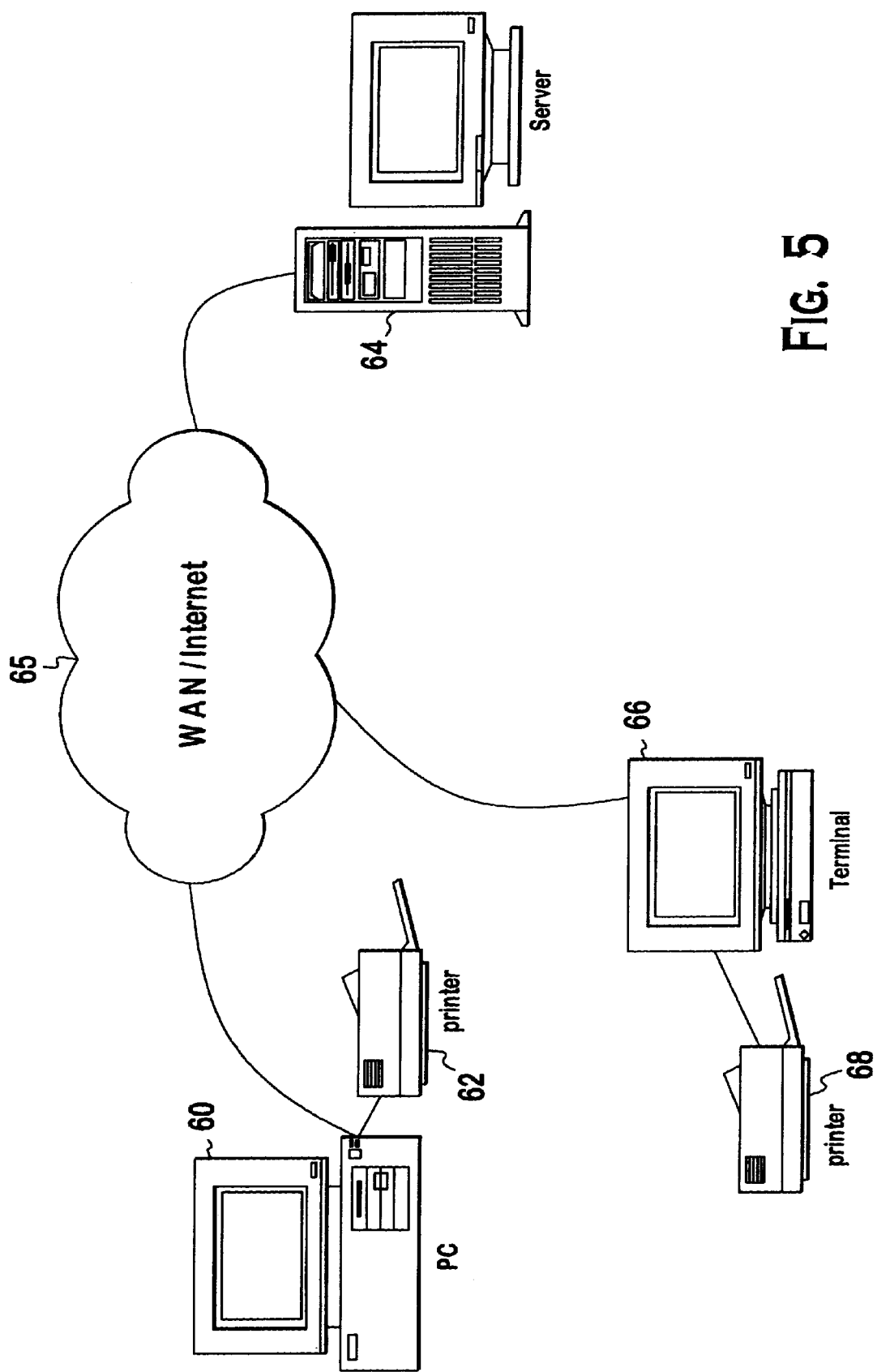
FIG. 5 is a diagram of the system according to the present invention.

Referring now to FIG. 5, the preferred system for performing this method includes a user terminal 66 where the information and measurements are input in steps 20, 22 and 24. The user terminal 66 may include a personal computer 60 or other device, which is capable of transmitting and receiving information. This information and measurement data is preferably transmitted over the Internet 65 to a server 64 or other suitable computing device for performing the calculations and checks in steps 28–44. Alternatively, the information and measurement data may be transmitted within a local area network, a wide area network, a wireless network, or within a computer or similar system. For example, the information and measurement data may be transmitted from a computer memory to a microprocessor in step 26. Conversely, transmission back to the user at step 46 is preferably conducted over the Internet 65 from the server 64 to the user terminal 66 or personal computer 60. Alternately, this transmission may be conducted as described above with respect to step 26. The output is preferably displayed at step 50 on a monitor. This output alternately may be supplied to a printer 62, 68 or other output device, and may be printed. Alternatively the output may be transmitted directly to a surgical device such as a laser for performing refractive surgery. Any one of these user devices can receive and/or display the output data. It should be understood by those reasonably skilled in the art that the method presented here is equally applicable to many different systems and the scope of this invention is not limited by the method's application to a particular system or hardware.

An advantage of the present invention is the precise surgical settings and recommendations are provided by this method requiring fewer surgical judgments and variables in creating a preoperative surgical plan. An additional advantage is that procedural recommendations are provided by the method along with cautions, which may lead to a recommendation that the procedure not be preformed. An additional advantage is that the method can be customized based on the collection and statistical analysis of preoperative data and post operative results from a given surgeon to achieve more consistent and desired procedure outcomes. Finally, an advantage of this procedure is that the surgical planning tool can be used over the Internet, in addition to more conventional means of data transfer.

The proposed invention addresses the problems of the prior art by suggesting an initial standardized technique and nomogram based on the results of other surgeons for the beginning surgeon. The calculations performed in this invention will be continually revised to accommodate new information about LASIK surgery. Even if newer generations of excimer lasers are programmed to directly calculate treatments for LASIK, the surgeon will always face patient variables that may influence surgical results. Consequently, surgeons will benefit from nomograms that can incorporate new information about parameters that can affect surgical results. This invention may assist the beginning surgeon in compiling data with the ultimate objective of creating a personalized nomogram. This process may be done via a number of methods, including through the Internet.

This invention helps to guide surgeon judgment and reduce variability by suggesting the depth of surgery and the plate depth. This would eliminate surgeon variability in the selection of plate depth for cutting the corneal flap by selecting the same plate depth in all cases with identical parameters. Additionally, the invention provides caution messages to avoid surgery on corneas that are too thin for the degree of refractive correction required based on the defined variables.

Other cautions based on changing industry standards such as a minimum patient age of 18 years, a minimum residual corneal stromal bed thickness of 250 microns, and a minimum Schirmer tear measurements of 4 millimeters are also provided. By excluding off-scale input by the use of value and range restricted drop down menus, the opportunity to operate on an inappropriate surgical candidate is reduced. Additionally, cautions are provided when based on a nomogram that takes into consideration refractive error and pupil size, as well as possibly optical zone, it is felt that based on industry standards, there is an increased risk of post operative glare. This alerts the surgeon to the potential of an adverse visual outcome based on a combination of what might otherwise be relatively low risk parameters.

Current standards offer only informal suggestions for collecting data on pre operative patient input and surgical outcomes. This invention allows for the collection and storage of patient input and, later, the collection and storage of operative results, in order to ultimately allow the surgeon to construct a customized nomogram that allows for continuing refinement and improvement of the refractive surgery results.

I claim:

1. A method of assisting in planning laser eye surgery comprising the steps of:
   collecting and entering eye measurements at a user location;
   transmitting the eye measurements from the user location to a computing device at a remote location;
   calculating a refraction setting for a corneal refractive surgery device;
   transmitting the refraction setting from the computing device to a user device; and,
   conducting tests on the collected eye measurements to provide a caution message along with the transmitted refraction setting.

2. The method of claim 1 wherein the refraction setting is calculated considering a patients refractive error and age.

3. The method of claim 2 wherein the refractive error and the age are weighted according to statistical analysis of surgeon data representative of a sample of surgeries.

4. The method of claim 1 wherein the measurements include a patient's age and manifest refraction.

5. The method of claim 4 further comprising the step of collecting doctor identification information.

6. The method of claim 4 further comprising the step of collecting basic patient information including a patient name, date of birth, date of surgery, dominant eye, monovision desired, and diopters of monovision.

7. The method of claim 6 wherein a patient age is calculated by subtracting the date of birth from the date of surgery.

8. The method of claim 7 wherein a test is conducted to compare the patient age to an age limit.

9. The method of claim 8 wherein a caution flag is set if the patient age is below the age limit.

10. The method of claim 9 wherein the age limit is 18 years.

11. The method of claim 1 wherein the measurements include a patient's vertex distance.

12. The method of claim 1 wherein the measurements include a patient's gender.

13. The method of claim 1 wherein the refraction setting includes a distance refraction setting.

14. The method of claim 1 wherein the refraction setting includes a near refraction setting.

15. The method of claim 1 wherein a test is conducted to determine a glare risk based on a pupil size and a refractive error.

16. The method of claim 1 wherein a caution message flag is set if the pupil size is greater than a pupil size limit.

17. The method of claim 16 wherein the pupil size limit is 5 mm.

18. The method of claim 1 wherein a test is conducted to compare refractive error, an optical zone, a corneal thickness and a plate depth thickness in order to compare residual stromal bed depth to an RSB limit.

19. The method of claim 18 wherein the refractive error includes monovision.

20. The method of claim 18 wherein a caution message flag is set if the residual stromal bed is less than the RSB limit for the given refractive error.

21. The method of claim 20 wherein the RSB limit is 250 microns.

22. The method of claim 1 wherein a test is conducted to compare a Shirmer tear production to a Shirmer limit.

23. The method of claim 22 wherein the Shirmer limit is 4 mm.

24. The method of claim 22 wherein a caution message flag is set if the Shirmer tear production is below the Shirmer limit.

25. The method of claim 1 wherein a recommended frequency rate is calculated.

26. The method of claim 25 wherein the recommended frequency rate is calculated by adding a constant to a product of a spherical equivalent refractive error and a second constant.

27. The method of claim 1 wherein a ring size is recommended based upon the corneal curvature.

28. The method of claim 27 wherein the corneal curvature is measured by a corneal topography.

29. The method of claim 27 wherein the corneal curvature is measured by keratometry.

30. The method of claim 1 wherein a treatment depth is recommended based upon a calculated anticipated residual corneal thickness.

31. The method of claim 30 wherein the treatment depth is calculated considering corneal pachmetry measurements, an estimated ablation depth, and an optical zone treatment size.

32. The method of claim 1 wherein an axis of refractive astigmatism is compared with an axis of corneal astigmatism.

33. The method of claim 32 wherein an astigmatism discrepancy error message flag is set when the axis of refractive astigmatism is greater than 20 degrees from the axis of corneal astigmatism.

34. The method of claim 1 wherein a magnitude of refractive astigmatism is compared with a magnitude of corneal astigmatism.

35. The method of claim 34 wherein an astigmatism discrepancy error message flag is set if an absolute difference in magnitude between the refractive astigmatism and the corneal astigmatism is greater than 1.5 diopters.

36. A system for assisting in surgery planning comprising:
an input device for receiving patient measurements;
a computing device for calculating surgical equipment settings from the patient measurements and statistical analysis of an individual surgeon data which is representative of a sample of surgeries previously performed by the individual surgeon; and,
a transmission device for passing the patient measurements and equipment settings between the input device and the computing device.

37. The system of claim 36 wherein the input device comprises a computer.

38. The system of claim 36 wherein the input device comprises a refractive surgical apparatus.

39. The system of claim 36 wherein the computing device comprises a server.

40. The system of claim 36 wherein the transmission device comprises a computer network.

41. The system of claim 40 wherein the computer network comprises the Internet.

42. A system for assisting in laser eye surgery planning comprising:
input means at a first location for receiving patient eye measurements;
computing means at a remote location for calculating a refraction setting for surgical laser equipment to be utilized during the surgery;
transmission means for transmitting the refraction setting from the computing device to a user device; and,
test means for conducting tests on the collected eye measurements to provide a caution message along with the transmitted distance refraction setting.

43. The system of claim 42 wherein the measurements include a patient's age and refractive error.

44. The system of claim 43 wherein doctor identification information is collected by the input means.

45. The system of claim 43 wherein basic patient information including date of birth, and date of surgery is collected by the input means.

46. The system of claim 45 wherein the computing means calculates a patient age by subtracting the date of birth from the date of surgery.

47. The system of claim 46 further comprising a test means for comparing the patient age to a limit.

48. The method of claim 47 further comprising an age caution flag means which is set if the patient age is below the limit.

49. The system of claim 43 wherein the computing means calculates a recommended frequency rate based upon the refractive error and a time required to perform this treatment.

50. The system of claim 42 wherein the measurements include a vertex distance.

51. The system of claim 42 wherein the measurements include a patient's gender.

52. The system of claim 51 wherein the refraction setting is calculated considering the refractive error and the age.

53. The system of claim 52 wherein the refractive error and the age are weighted according to statistical analysis of surgeon data representative of a sample of surgeries.

54. The system of claim 42 wherein the test means performs a comparison to compare pupil size and refractive error.

55. The system of claim 54 further comprising a pupil size caution message flag means which is set if the pupil exceeds a pupil size limit for a given refractive error and optical treatment zone.

56. The system of claim 42 wherein the test means compares the refractive error, an optical zone, a corneal thickness and a calculated flap thickness.

57. The system of claim 56 further comprising a corneal thickness caution message flag means which is set if the cornea is too thin for a given refractive error, optical treatment zone and plate depth based upon a calculation of a residual stromal bed.

58. The system of claim 42 wherein the test means performs a comparison to compare a Shirmer tear production to a limit.

59. The system of claim 58 further comprising a dry eye caution message flag means, which is set if the Shirmer tear production is below the limit.

60. The system of claim 42 wherein the computing means determines a recommended ring size based upon corneal flatness or steepness.

61. The system of claim 42 wherein the computing means determines a plate thickness recommendation based upon an initial corneal thickness measurement, an estimated ablation depth based on refractive error, an optical treatment zone, and industry standards for residual corneal bed thickness following treatment.

62. The method of claim 42 wherein an axis of refractive astigmatism is compared with an axis of corneal astigmatism.

63. The method of claim 62 wherein an astigmatism discrepancy error message flag is set when the axis of refractive astigmatism is greater than 20 degrees from the axis of corneal astigmatism.

64. The method of claim 42 wherein a magnitude of refractive astigmatism is compared with a magnitude of corneal astigmatism.

65. The method of claim 63 wherein an astigmatism discrepancy error message flag is set if an absolute difference in magnitude between the refractive astigmatism and the corneal astigmatism is greater than 1.5 diopters.

* * * * *